(12) United States Patent
Sun

(10) Patent No.: US 6,408,208 B1
(45) Date of Patent: Jun. 18, 2002

(54) FULLY AUTOMATIC AND PHYSIOLOGIC RATE-ADAPTIVE PACING

(75) Inventor: Weimin Sun, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/428,831

(22) Filed: Oct. 28, 1999

(51) Int. Cl.$^7$ ............................................. A61N 1/365
(52) U.S. Cl. ........................ 607/17; 607/19; 607/20; 600/513
(58) Field of Search ........................ 607/17, 18, 19, 607/20; 600/513

(56) References Cited

U.S. PATENT DOCUMENTS

| | | | |
|---|---|---|---|
| 4,884,576 A | 12/1989 | Alt | 128/419 PG |
| 4,901,726 A | 2/1990 | Hansen | 128/419 PG |
| 5,044,366 A * | 9/1991 | Alt | 607/17 |
| 5,226,413 A | 7/1993 | Bennett et al. | 128/419 |
| 5,231,986 A | 8/1993 | Bennett | 607/11 |
| 5,292,340 A | 3/1994 | Crosby et al. | 607/17 |
| 5,360,436 A | 11/1994 | Alt et al. | 607/18 |
| 5,372,607 A | 12/1994 | Stone et al. | 607/30 |
| 5,376,106 A | 12/1994 | Stahmann et al. | 607/18 |
| 5,476,483 A | 12/1995 | Bornzin et al. | 607/17 |
| 5,487,753 A * | 1/1996 | MacCarter et al. | 607/17 |
| 5,514,162 A | 5/1996 | Bornzin et al. | 607/19 |
| 5,562,711 A | 10/1996 | Yerich et al. | 607/17 |
| 5,626,622 A * | 5/1997 | Cooper | 607/18 |
| 5,645,575 A | 7/1997 | Stangl et al. | 607/17 |
| 5,649,968 A | 7/1997 | Alt et al. | 607/19 |
| 5,690,687 A | 11/1997 | Hansen | 607/17 |
| 5,792,198 A | 8/1998 | Nappholz et al. | 607/18 |
| 5,800,470 A | 9/1998 | Stein et al. | 607/20 |
| 5,843,139 A | 12/1998 | Goedeke et al. | 607/32 |
| 5,931,858 A | 8/1999 | Kadhiresan et al. | 607/20 |
| 5,974,340 A | 10/1999 | Kadhiresan | 607/18 |
| 5,978,711 A | 11/1999 | van Hove | 607/17 |
| 6,055,454 A | 4/2000 | Heemels | 607/18 |

FOREIGN PATENT DOCUMENTS

| | | | |
|---|---|---|---|
| EP | 0798014 | 9/1986 | A61N/1/365 |
| EP | 0702980 | 9/1994 | A61N/1/365 |

* cited by examiner

Primary Examiner—Carl Layno
(74) Attorney, Agent, or Firm—Schwegman, Lundberg, Woessner & Kluth, P.A.

(57) ABSTRACT

Methods and apparatus for automatic estimation of output mapping parameters for a control system where those output mapping parameters may be estimated from changes in sensor input data when the control system enters steady-state motion. Methods and apparatus for automatic estimation of minute ventilation at anaerobic threshold and minute ventilation at peak exercise for adjustment of rate-adaptive curves of pacemakers. The methods include detecting steady-state motion of the pacemaker and calculating minute ventilation at anaerobic threshold and minute ventilation at peak exercise from changes in minute ventilation sensor data corresponding to the period of steady-state motion.

30 Claims, 9 Drawing Sheets

FULLY AUTOMATIC AND PHYSIOLOGIC RATE-ADAPTIVE PACING

TECHNICAL FIELD

The invention relates generally to a system for automatic estimation of output mapping parameters and particularly, but not by way of limitation, to methods and apparatus for automatic estimation of $MV_{AT}$ and $MV_{PEAK}$ parameters of rate-adaptive pacing curves.

BACKGROUND

Many control systems rely on an output mapping to convert a measured control input to a desired control output. The output mapping is a graphical, tabular or other mathematical function of control output versus control input. As an example, a burner system with fuel and oxygen feeds may measure fuel feed rate as a control input and utilize output mapping to define the desired oxygen feed rate as a control output. The output mapping of oxygen feed rate versus fuel feed rate may not be linear, e.g., requiring increasing levels of excess oxygen at higher fuel feed rates to provide efficient burning of the fuel. While theoretical considerations allow designers to calculate an output mapping of the desired control output as a function of the control input, one or more of the parameters in the calculations may be empirical, i.e., based on experience or observations as opposed to theory or conjecture. Testing of the control system may be required to define the empirical parameters for proper operation of the control system. Another example of control systems utilizing output mapping are some cardiac rhythm management systems.

Cardiac rhythm management systems include, among other things, pacemakers, also referred to as pacers. Pacemakers deliver timed sequences of low energy electrical stimuli, called pace pulses, to the heart, such as via a transvenous leadwire having one or more electrodes disposed in the heart. Heart contractions are initiated in response to such pace pulses. By properly timing the delivery of pace pulses, the heart can be induced to contract in proper rhythm, greatly improving its efficiency as a pump. Pacemakers are often used to treat patients with bradyarrhythmias, that is, hearts that beat too slowly, or irregularly.

There exists a class of pacemakers known as variable rate or rate-adaptive pacemakers which include a physiologic sensor indicative of metabolic demand and a variable rate pulse generator responsive to changes in metabolic demand. Some physiologic sensors for determining metabolic demand include minute ventilation (MV) sensors for measuring trans-thoracic impedance variations and generating an output signal varying as a function of the patient's minute ventilation, and accelerometers for measuring body vibration during physical activity and generating an output signal varying as a function of the patient's movement. Accelerometers are typically filtered and processed such that the resulting output signal is indicative of the patient's exercising activity, and not of external vibration sources or internal noise. Other physiologic sensors are used, e.g., blood pH, blood temperature, QT interval, blood oxygen saturation, respiratory rate and others.

Rate-adaptive pacemakers attempt to pace a patient's heart at a rate corresponding to the patient's metabolic demand. They accomplish this by utilizing an output mapping to convert a given physiologic sensor input to a unique output signal level. Although many of the physiologic sensors are highly correlated to metabolic demand, this correlation may be empirical in nature, thus making it difficult to determine the appropriate output mapping prior to implantation of the pacemaker. If the patient's actual metabolic demand differs from the predetermined output mapping, the paced rate will be either too high or too low. If the paced rate is too high, the patient may feel palpitated or stressed. If too low, the patient may feel fatigued, tired or dizzy.

As will be seen from the above concerns, there exists a need for an improved method of tuning output mapping. The above-mentioned problems with matching pacing to a patient's metabolic demand and other problems are addressed by the present invention and will be understood by reading and studying the following specification.

SUMMARY

One embodiment includes a method of adjusting an output mapping of a control output versus a control input for a control system. The method includes collecting first signal input data from a first sensor indicative of motion of the control system, collecting second signal input data from a second sensor, and storing the first and second signal input data in a memory, thereby producing stored first signal input data and stored second signal input data. The method further includes detecting steady-state motion of the system from the stored first signal input data, calculating at least one parameter for the output mapping in response to changes in the stored second signal input data during a period of steady-state motion, thereby producing at least one calculated parameter, and adjusting the output mapping in response to the at least one calculated parameter. In another embodiment, collecting first signal input data from a first sensor includes collecting first signal input data from an accelerometer. In a further embodiment, detecting steady-state motion of the system includes subjecting the stored first signal input data to Fourier analysis to convert the stored first signal input data to its harmonically-related frequency components.

Another embodiment includes a method of adjusting a rate-adaptive curve of a pacemaker. The method includes collecting first signal input data from a first sensor indicative of motion of the pacemaker, collecting second signal input data from a minute ventilation sensor, and storing the first and second signal input data in a memory, thereby producing stored first signal input data and stored second signal input data. The method further includes detecting steady-state motion of the pacemaker from the stored first signal input data, calculating at least one parameter for the rate-adaptive curve in response to changes in the stored second signal input data during a period of steady-state motion, thereby producing at least one calculated parameter, and adjusting the rate-adaptive curve in response to the at least one calculated parameter. In a further embodiment, collecting first signal input data from a first sensor includes collecting first signal input data from an accelerometer. In a still further embodiment, detecting steady-state motion of the pacemaker includes subjecting the stored first signal input data to Fourier analysis to convert the stored first signal input data to its harmonically-related frequency components. In one embodiment, detecting steady-state motion of the pacemaker includes detecting steady-state motion when the frequency components exhibit an amplitude maxima at a frequency component in the range of about 1 to 4 Hertz.

A further embodiment includes a method of adjusting a two-slope rate-adaptive curve of a pacemaker, wherein the two-slope rate-adaptive curve is defined by parameters including minute ventilation at anaerobic threshold and minute ventilation at peak exercise. The method includes collecting first signal input data from an accelerometer, collecting second signal input data from a minute ventilation sensor, and storing the first and second signal input data in a memory, thereby producing stored first signal input data and stored second signal input data. The method further includes detecting steady-state motion of the pacemaker from the stored first signal input data by subjecting the stored first signal input data to Fourier analysis, calculating the minute ventilation at anaerobic threshold and minute ventilation at peak exercise in response to changes in the stored second signal input data, and adjusting the rate-adaptive curve in response to the calculated minute ventilation at anaerobic threshold and the calculated minute ventilation at peak exercise.

Yet another embodiment includes a control system. The control system includes a processor, a memory coupled to the processor and having output mapping data stored thereon defining an output mapping, and a regulator coupled to the processor. The control system further includes a first sensor input coupled to the processor and adapted to receive first sensor input data indicative of motion of the control system, a second sensor input coupled to the processor and adapted to receive second sensor input data, a control output coupled to the regulator, and a detection module coupled to the processor and adapted to detect steady-state motion of the control system in response to the first sensor input data. The processor is adapted to adjust the output mapping data in response to changes in the second sensor input data when the detection module detects steady-state motion of the control system.

One embodiment includes a rate-adaptive pacemaker. The rate-adaptive pacemaker includes a processor, a memory coupled to the processor and having output mapping data stored thereon defining a rate-adaptive curve, and a variable-rate pulse generator coupled to the processor. The rate-adaptive pacemaker further includes a first sensor input coupled to the processor and adapted to receive first sensor input data indicative of motion of the pacemaker, a second sensor input coupled to the processor and adapted to receive second sensor input data from a minute ventilation sensor, a pulse output coupled to the variable-rate pulse generator, and a detection module coupled to the processor and adapted to detect steady-state motion of the pacemaker in response to the first sensor input data. The processor is adapted to adjust the output mapping data in response to changes in the second sensor input data when the detection module detects steady-state motion of the pacemaker. In another embodiment, the rate-adaptive pacemaker further includes an accelerometer coupled to the first sensor input to provide the first sensor input data.

Another embodiment includes a rate-adaptive pacemaker. The rate-adaptive pacemaker includes a processor, a memory coupled to the processor and having output mapping data stored thereon defining a rate-adaptive curve, and a variable-rate pulse generator coupled to the processor. The rate-adaptive pacemaker further includes a first sensor input coupled to the processor, a second sensor input coupled to the processor, and a pulse output coupled to the variable-rate pulse generator. The memory has instructions stored thereon capable of causing the processor to perform a method. The method includes collecting first signal input data from a first sensor indicative of motion of the pacemaker at the first sensor input, collecting second signal input data from a minute ventilation sensor at the second sensor input, and storing the first and second signal input data in the memory, thereby producing stored first signal input data and stored second signal input data. The method further includes detecting steady-state motion of the pacemaker from the stored first signal input data, calculating at least one parameter for the rate-adaptive curve in response to changes in the stored second signal input data during a period of steady-state motion, thereby producing at least one calculated parameter, and adjusting the output mapping data in response to the at least one calculated parameter. In a further embodiment, collecting first signal input data from a first sensor comprises collecting first signal input data from an accelerometer.

Other embodiments include methods and apparatus of varying scope.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the invention. The following detailed description is, therefore, not to be taken in a limiting sense, and the scope of the invention is defined by the appended claims and their equivalents. Like numbers in the figures refer to like components, which should be apparent from the context of use.

The following description will be illustrated in the context of a rate-adaptive pacemaker. Those skilled in the art will recognize that the methods and apparatus described herein can be adapted for use in other systems seeking to generate output mapping using empirical parameters where the value of those empirical parameters can be predicted through normal use of the system.

Figure 1:
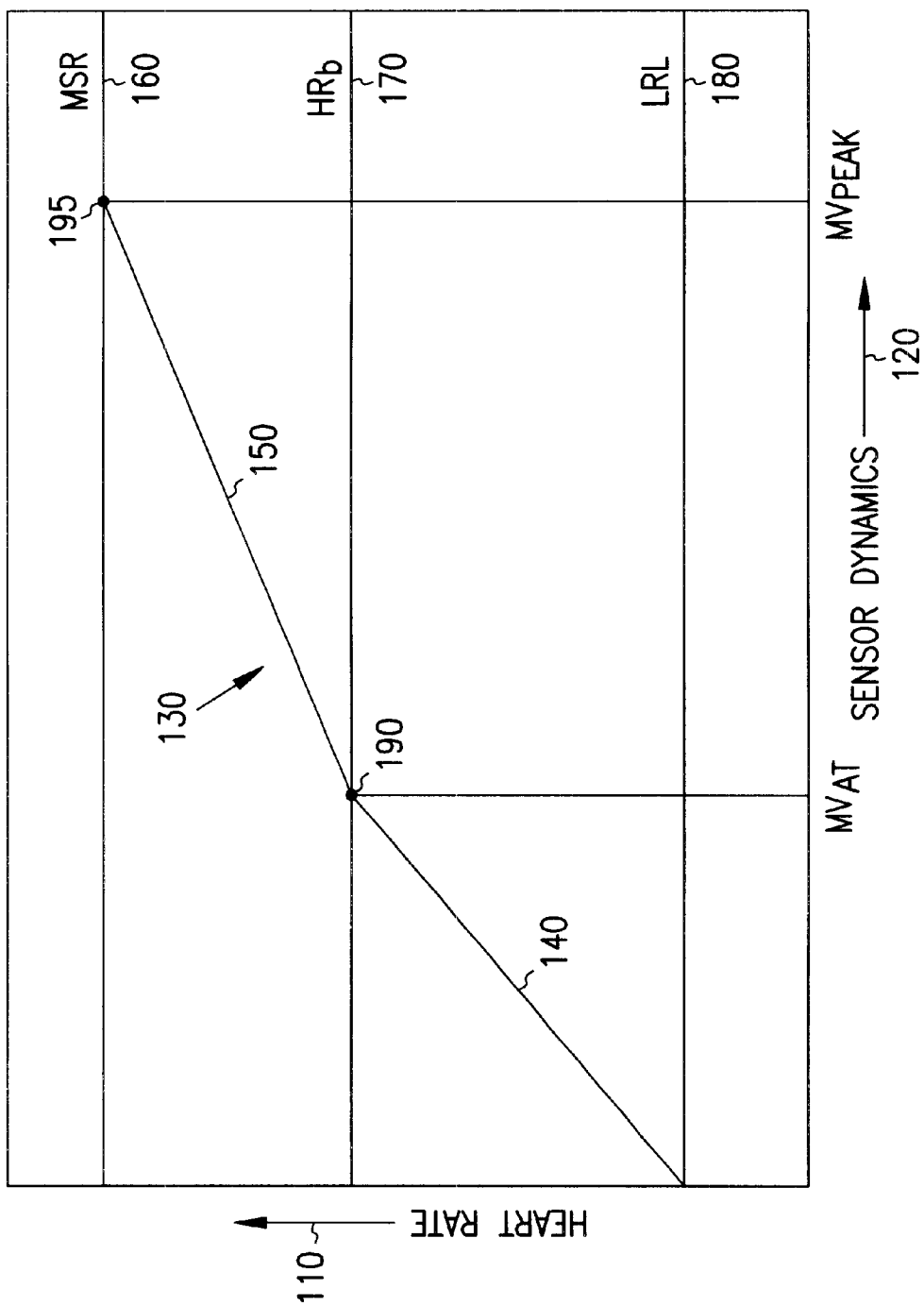
FIG. 1 is a graph of a two-slope rate-adaptive curve.

Current rate-adaptive pacemakers automatically raise the pacing rate, i.e., the control output, of an exercising patient in response to the physiologic sensor, i.e., the control input, often by utilizing an output mapping referred to as a rate-adaptive curve. These rate-adaptive curves may take the form of a two-slope curve. FIG. 1 is graph representative of a two-slope rate-adaptive curve 130, plotting desired heart rate as a function of the physiologic sensor input. In the graph of FIG. 1, heart rate is increasing in the direction of arrow 110 and the sensor signal amplitudes are increasing in the direction of arrow 120. Increasing sensor signal amplitudes are indicative of a higher activity level of the patient.

Rate-adaptive curve 130 includes an aerobic response portion 140 and an anaerobic response portion 150. It is common that the two response portions 140 and 150 meet at the sensor value indicative of the patient reaching the anaerobic threshold, or an activity level where oxygen use exceeds oxygen intake. When using an MV sensor as the physiologic sensor, this point is termed the MV at anaerobic threshold or $MV_{AT}$. The two response portions 140 and 150 further meet at a heart rate at breakpoint or HRb. HRb is shown as line 170 and ideally represents the desired heart rate at the anaerobic threshold. Response portion 140 terminates, or has a lower endpoint, at a lower rate limit (LRL) represented by line 180. LRL is the minimum pacing rate regardless of sensor input. Response portion 150 terminates, or has an upper endpoint, at a maximum sensor rate (MSR) represented by line 160. MSR is the maximum pacing rate driven by sensor input. When using an MV sensor as the physiologic sensor, this endpoint further occurs at the MV at peak exercise or $MV_{PEAK}$.

Aerobic response portion 140 has a first slope, often defined by an aerobic response factor (ARF). Anaerobic response portion 150 has a second slope, often defined by a high heart-rate response factor (HHRRF). Using this two-slope rate-adaptive curve 130, a physiologic sensor input is converted to a desired heart rate or pacing rate. Other forms of rate-adaptive curves, such as linear curves having more or fewer response portions or some non-linear curve, are also capable of performing the output mapping function, i.e., converting a physiologic sensor input into a desired pacing rate. Further, conversion of control input to control output can be accomplished via a look-up table or other non-graphical representation of an output mapping. As can be seen in FIG. 1, aerobic response portion 140 and anaerobic response portion 150 of rate-adaptive curve 130 are highly dependent upon the assumed $MV_{AT}$ and $MV_{PEAK}$. Their accuracy, therefore, is dependent upon an accurate estimation of the true $MV_{AT}$ and $MV_{PEAK}$.

Although the various embodiments will be described with reference to a two-slope rate-adaptive curve such as depicted in FIG. 1, the invention is not so limited in its application. Those skilled in the art will recognize that the methods disclosed herein are adaptable to a variety of conversion methods and output mapping curves. The embodiments described herein may be adapted to any output mapping that is defined, at least in part, using one or both of the parameters of $MV_{AT}$ and $MV_{PEAK}$.

Regardless of the conversion method from MV sensor input to pacing output, rarely are the patient's true MV dynamics known at the time of implant of the pacemaker. Despite this lack of information, the rate-adaptive curve must be programmed for the pacemaker to function properly, e.g., the parameters of MSR, LRL, HRb, ARF and HHRRF have to be specified. Without true $MV_{AT}$ and $MV_{PEAK}$, these empirical parameters may not define a rate-adaptive curve that matches a patient's metabolic need.

Differences between the output mapping generated at implantation and the patient's metabolic need result in over-responsive or under-responsive pacing. Over-responsive pacing results from a paced heart rate exceeding the metabolic need. Over-responsive pacing generally results in a patient experiencing palpitation or stress. Under-responsive pacing results from a deficit between the paced heart rate and the metabolic need. Under-responsive pacing generally results in a patient experiencing fatigue, tiredness or dizziness.

Some have postulated that an appropriate pacing rate or heart rate (HR) could be calculated at any level of metabolic demand if the true MV at anaerobic threshold ($MV_{AT}$) and peak exercise ($MV_{PEAK}$) were known. Determination of true $MV_{AT}$ and $MV_{PEAK}$ has often relied upon maximal exertion testing of the patient, which is costly, time-consuming and stressful. It has been shown by Kay et al. in U.S. patent application Ser. No. 09/408,623, titled Method of Determining a Ventilatory Threshold Breakpoint for an Adaptive Rate Pacemaker and commonly assigned (hereinafter "Kay et al."), that knowledge of respiratory rate (RR) and tidal volume (TV) from onset of exercise to steady-state, along with MV at rest, can be used to predict $MV_{AT}$ and $MV_{PEAK}$ without maximal testing. The application of Kay et al. is herein incorporated by reference for its methods of predicting $MV_{AT}$ and $MV_{PEAK}$. Accurate prediction of $MV_{AT}$ and $MV_{PEAK}$ allow calculation of metabolic reserve and HR at any intermediate exercise workload.

As Kay et al. have shown, accurate approximations of $MV_{AT}$ and $MV_{PEAK}$ may be calculated from the observation of steady-state exercise of a patient and changes in the respiratory parameters. While this permits physicians to more accurately program pacemakers without the need for maximal exertion testing, prediction alone does not eliminate physician involvement in performing and monitoring the submaximal exertion testing.

Figure 2:
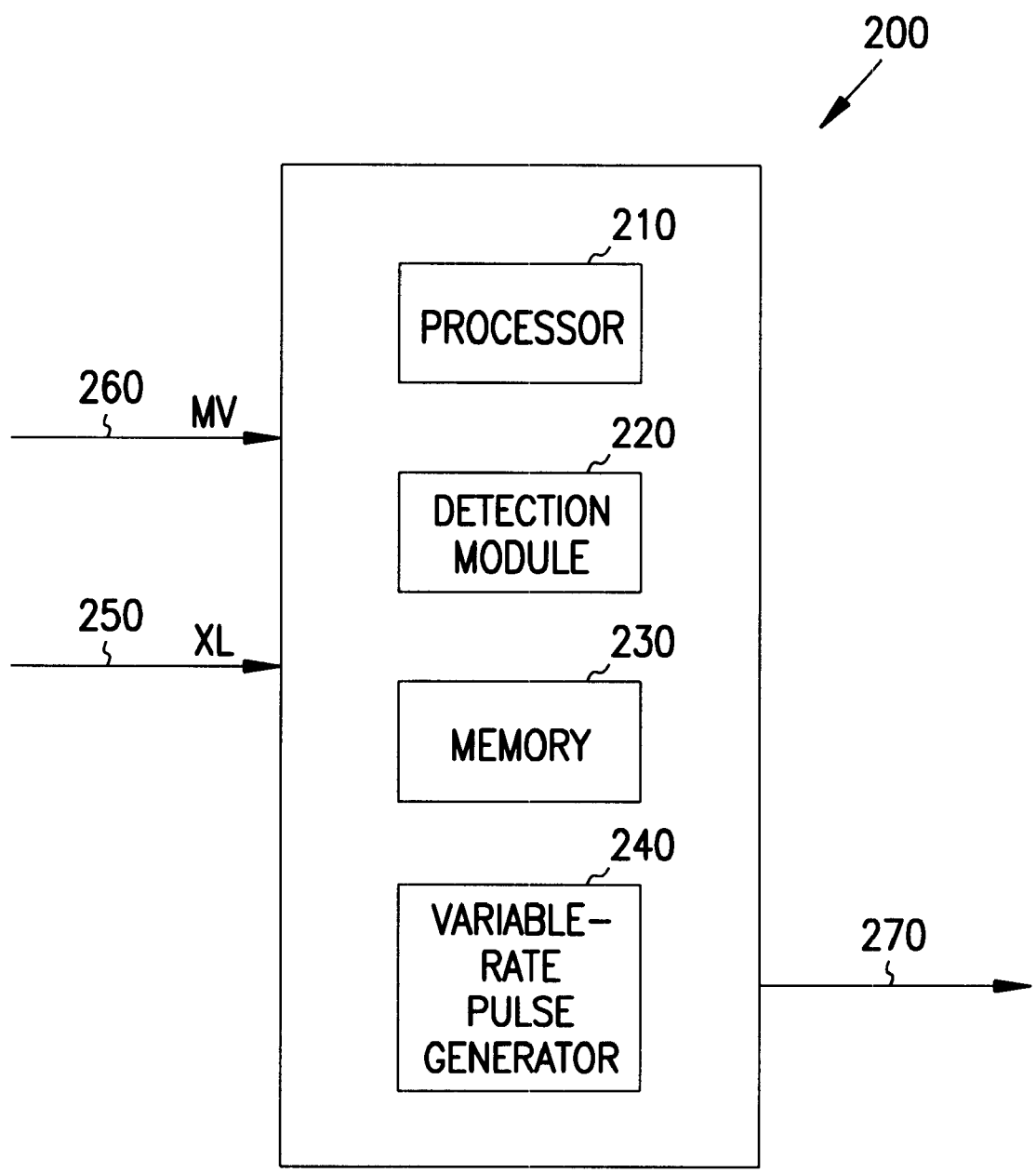
FIG. 2 is a block diagram of one embodiment of a pacemaker.

FIG. 2 is a block diagram of one embodiment of a pacemaker 200. It will be recognized by those skilled in the art that pacemaker 200 may include other components, but that FIG. 2 has been simplified to focus on aspects of the invention. Pacemaker 200 includes a processor 210, a memory 230 coupled to processor 210, and a variable-rate pulse generator 240, or regulator, coupled to processor 210. Processor 210 will be understood to represent a single processor or a plurality of cooperating processors.

Pacemaker 200 further has a detection module 220 coupled to processor 210. Pacemaker 200 still further includes a first physiologic sensor input 250, in this example an accelerometer (XL) sensor input, and a second physiologic sensor input 260, in this example an MV sensor input. The XL sensor is preferably located physically within pacemaker 200. In one embodiment, first physiologic sensor input 250 and second physiologic sensor input 260 are the same sensor input, thus providing both an indication of metabolic demand and an indication of steady-state motion. To provide the pacing to the patient's heart, pacemaker 200 also includes a pulse output 270.

Memory 230 provides storage for historical data as well as data capable of defining an output mapping. In one embodiment, the output mapping includes a rate-adaptive curve defined by parameters including $MV_{AT}$ and $MV_{PEAK}$. The parameters defining the output mapping, or the rate-adaptive curve, are the output mapping data. Memory 230 is generally some form of machine-readable medium such as random-access memory (RAM), read-only memory (ROM) or flash memory. Memory 230 further contains instructions stored thereon capable of causing processor 210 to carry out processing tasks. Memory 230 may be a combination of more than one type of memory, e.g., ROM or flash memory for instructions to the processor and RAM for historical data and data defining the output mapping.

Processor 210 receives input from physiologic sensor inputs 250 and 260. Processor 210 samples, processes and stores historical data in memory 230. Processor 210 tunes the data defining the rate-adaptive curve in response to the historical data from physiologic sensor inputs 250 and 260 as described below. Processor 210 further utilizes the second physiologic sensor input 260 and the data defining the rate-adaptive curve to cause variable-rate pulse generator 240 to generate a signal on pulse output 270, thus providing desired pacing to the patient's heart Detection module 220 utilizes input from the first physiologic sensor input 250 to detect steady-state motion of the pacemaker, which is directly related to steady-state exercise of the patient. In one embodiment, detection module 220 is a software module, such as instructions stored on memory 230 capable of causing processor 210 to carry out a method of detecting steady-state motion of the pacemaker. In another embodiment, detection module 220 is a dedicated processor hard-coded to carry out a method of detecting steady-state motion of the pacemaker, such as an application-specific integrated circuit (ASIC).

Steady-state exercise of the patient generally results in steady-state motion of the pacemaker. Conversely, steady-state motion of the pacemaker is indicative of steady-state exercise of the patient. In the embodiment utilizing an XL sensor for the first physiologic sensor input 250, steady-state motion is indicated by a substantially constant frequency and amplitude of the sensor input data from the XL sensor. While the term "substantially constant" implies some regularity in the frequency and amplitude, the user is allowed some latitude. It should be noted, however, that increasing regularity of the frequency and amplitude is indicative of increasingly steady motion of the pacemaker and is thus more indicative of steady-state exercise of the patient.

Detection of steady-state motion is made possible using an XL sensor due to the characteristic signal trace of such motion of the pacemaker. FIGS. 3A–3D help illustrate this characteristic signal trace by observing a variety of situations. In each situation, an XL sensor is attached to a patient and the resulting signal trace is expected to be representative of the motion an implanted pacemaker would experience in that situation. While each signal trace is exemplary only, and repeated testing in substantially similar situations will likely result in variations in the resulting signal traces, FIGS. 3A–3D are useful in demonstrating the characteristic differences of steady-state motion indicative of steady-state exercise of a patient.

Figure 3A:
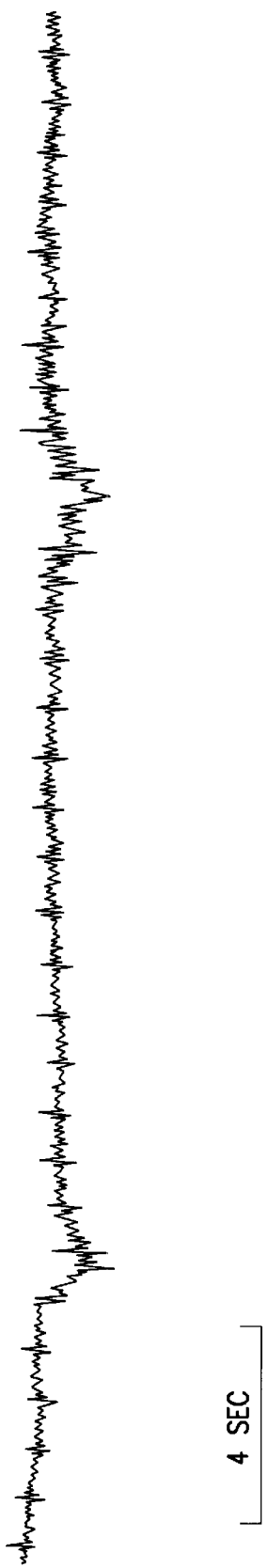
FIGS. 3A–3D are sample signal traces from an accelerometer.

FIG. 3A is a sample signal trace from an XL sensor with a patient driving in a car. The trace in FIG. 3A exhibits a small amplitude, indicative of only minor motion variation of the XL sensor and thus only minor motion of the pacemaker relative to the patient. Such a trace generally would not be indicative of motion of the pacemaker sufficient to indicate exercise of the patient.

It is recognized that some forms of exercising, e.g., bicycling, may result in only minor motion of the pacemaker relative to the patient. To detect steady-state exercise of the patient in situations where the motion of the pacemaker relative to the patient is insufficient to indicate such exercise, another sensor type may be required. One example may be impedance measurement of major muscle groups.

Figure 3B:
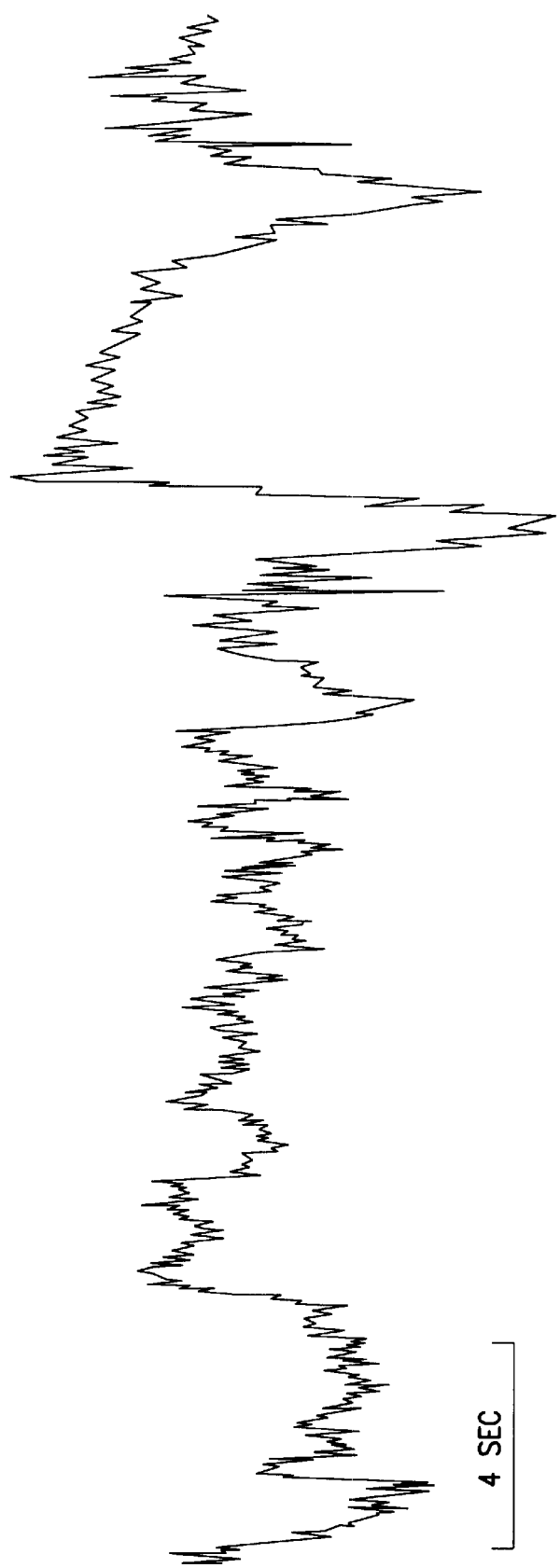

FIG. 3B is a sample signal trace from an XL sensor with a patient walking down stairs. As can be seen in FIG. 3B, the signal trace is irregular in both frequency and amplitude. Such a trace generally would not be indicative of steady-state motion of the pacemaker, nor would it generally be indicative of steady-state exercise of the patient.

Figure 3C:
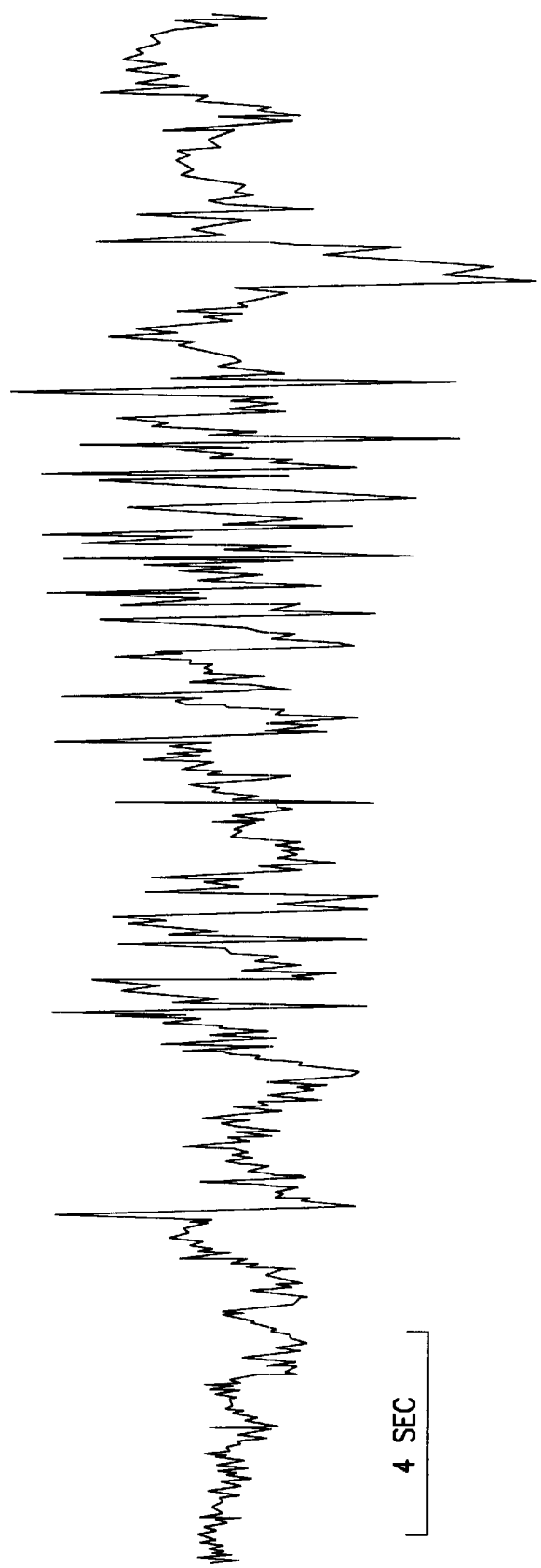

FIG. 3C is a sample signal trace from an XL sensor with a patient walking through the halls of a building. As with FIG. 3B, the signal trace is less regular in both frequency and amplitude. Such a trace generally would not be indicative of steady-state motion of the pacemaker, nor would it generally be indicative of steady-state exercise of the patient.

Figure 3D:
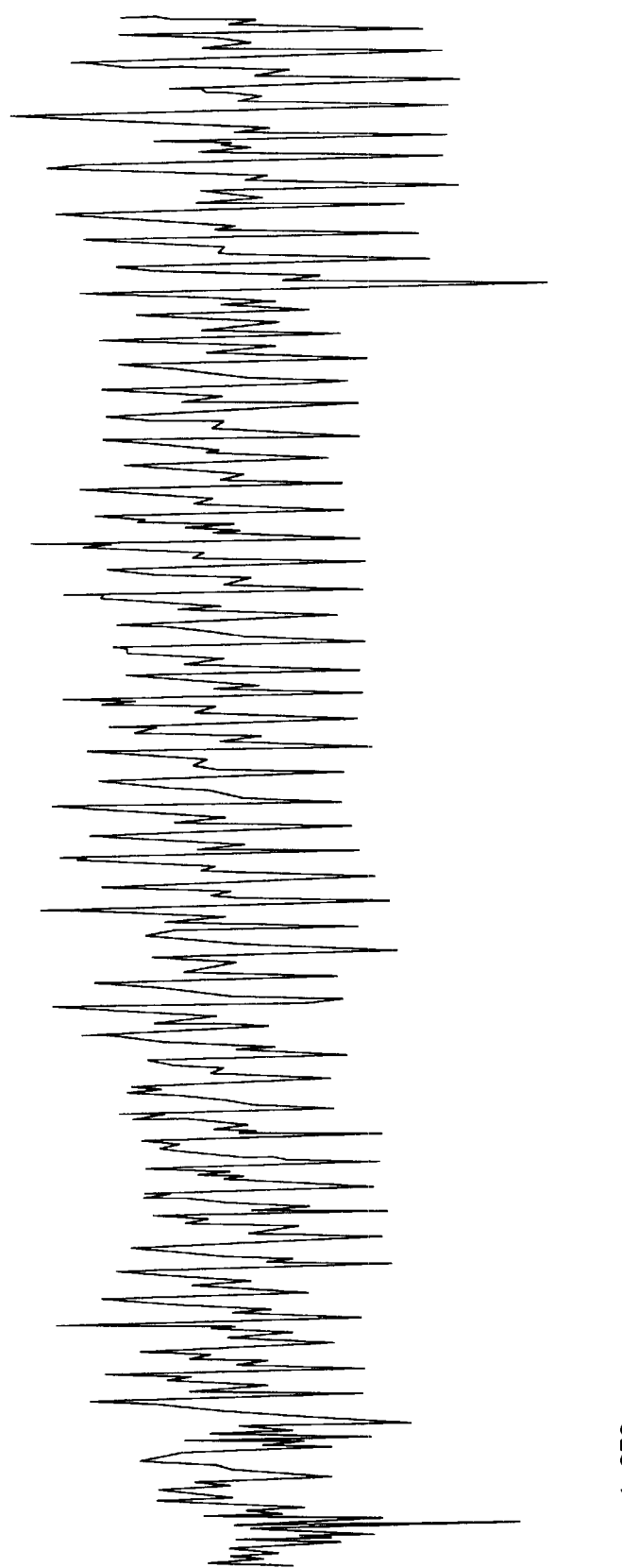

FIG. 3D is a sample signal trace from an XL sensor with a patient walking on a treadmill. As can be seen in FIG. 3D, the signal trace exhibits a characteristic regularity in both frequency and amplitude. Such a trace with regularity in both frequency and amplitude generally would be indicative of steady-state motion of the pacemaker and, thus, steady-state exercise of the patient.

While detecting the characteristic signal trace indicating steady-state motion of the pacemaker from a visual signal trace is useful for comparative purposes, the embodiments of the detection module 220 detect the characteristic signal trace from an electrical waveform from a physiologic sensor at the first physiologic sensor input 250. In one embodiment, detection module 220 digitizes the electrical waveform. The digitized waveform data is then calibrated as to amplitude and subjected to Fourier analysis, such as fast Fourier transform (FFT), to convert the digitized waveform data to its harmonically-related frequency components. Signal traces indicative of steady-state motion of the pacemaker indicating steady-state exercise of the patient will generally have a pronounced amplitude maxima corresponding to a frequency component in the range of about 1 to 4 Hz.

Figure 4:
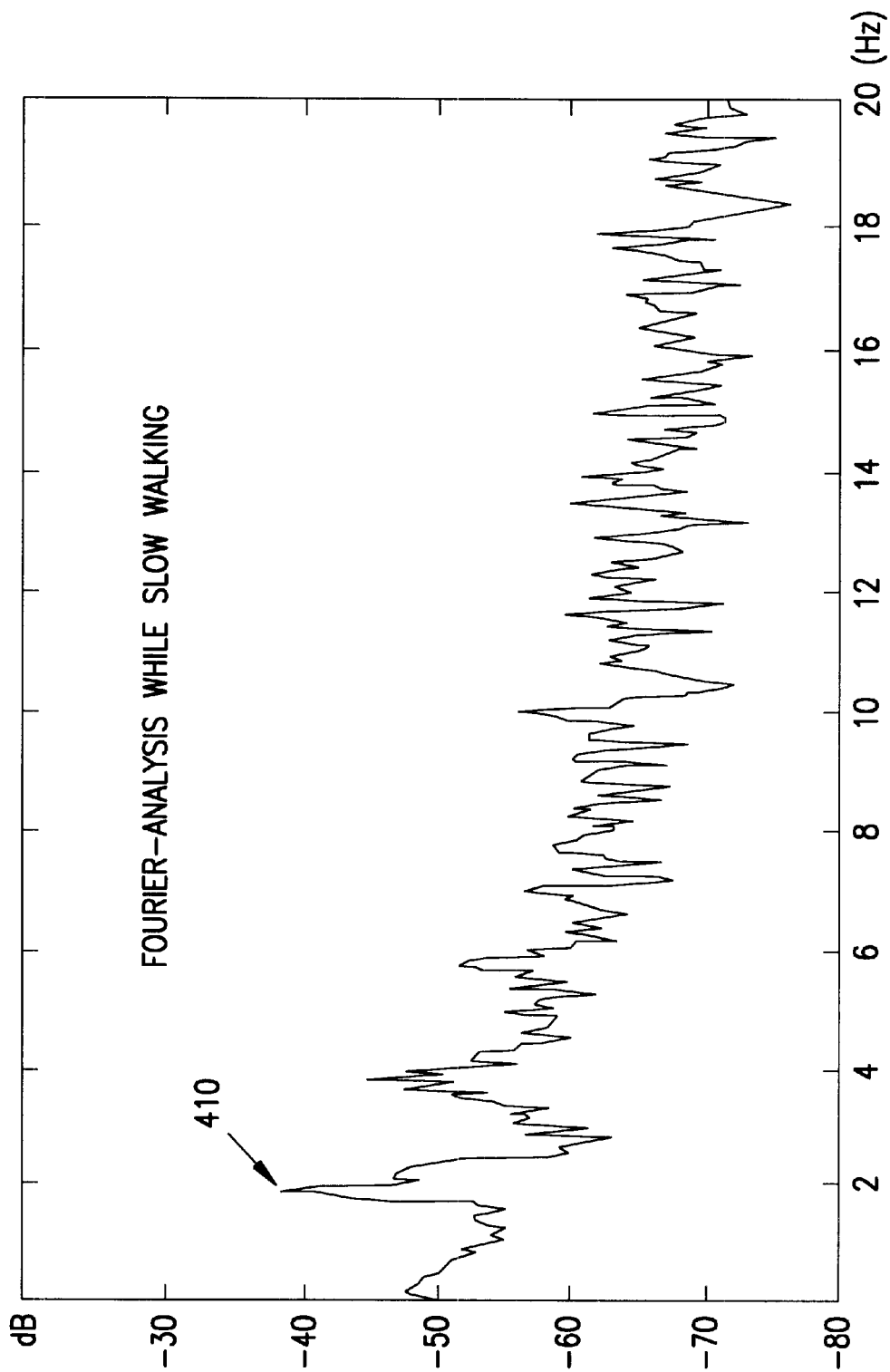
FIG. 4 is a plot of a Fourier analysis of the electrical waveform from an accelerometer.

FIG. 4 is an example plot of a Fourier analysis of the electrical waveform from an XL sensor while a patient walks slowly. FIG. 4 is plotted with amplitude in decibels as a function of frequency in hertz. As shown in FIG. 4, there is a pronounced amplitude maxima 410 corresponding to a frequency component at about 2 Hz. In one embodiment, an amplitude maxima of a frequency component between about 1 and 4 Hz is indicative of steady-state motion of the pacemaker and steady-state exercise of the patient.

In addition to amplitude maxima, other criteria may be introduced to further define steady-state motion indicative of steady-state exercise. As an example, integration of the function of amplitude versus frequency following Fourier analysis may be used to evaluate the ratio of power of frequency components surrounding the amplitude maxima to power of the remaining frequency components, herein referred to as the power ratio. In this example, the detection module 220 may not indicate steady-state motion unless a minimum predetermined power ratio is reached. In one embodiment, the minimum power ratio is 2 for a frequency range of ±0.5 Hz from the amplitude maxima. In a further embodiment, the minimum power ratio is 3 for a frequency range of ±0.5 Hz from the amplitude maxima. Increasing power ratios at a given frequency range and decreasing frequency ranges at a given power ratio are indicative of increasingly steady motion of the pacemaker and are thus more indicative of steady-state exercise of the patient.

Improved signal quality, and accompanying improvements in detecting steady-state motion, can be obtained by employing high-pass and low-pass filtering techniques to restrict the frequencies of the data from the physiologic sensor. As an example, the electrical waveform from an XL sensor may be filtered to remove frequencies below about 0.3 Hz and above about 5 Hz.

The pacemaker has been described in the context of using an XL sensor at the first physiologic sensor input. An XL sensor is the preferred physiologic sensor for detecting steady-state motion as it can be contained within the pacemaker, requires no separate external connection and is thus minimally intrusive. However, other sensors may be used to detect steady-state exercise of the patient. As an example, impedance measurements may be taken of one or more major muscle groups as an indication of exercise. The signal trace of impedance measurements of a major muscle group would be analyzed for steady-state exercise in like fashion to the analysis of the accelerometer signal traces, where increasing regularity in frequency and amplitude is indicative of steady-state exercise. Any sensor capable of directly indicating exercise of the patient or indirectly indicating exercise of the patient, e.g., motion of the pacemaker, may be used as input to the first physiologic sensor input.

Processor 210 may estimate $MV_{AT}$ and $MV_{PEAK}$ utilizing the calculations as proposed by Kay et al. in response to detection module 220 indicating the start of steady-state exercise. As noted previously, Kay et al. conclude that changes in TV at the onset of exercise allow accurate prediction of the $MV_{AT}$ and $MV_{PEAK}$. An MV signal can be obtained by measuring transthoracic (across the chest or thorax) impedance. Transthoracic impedance provides respiratory information, including how fast (respiratory rate; RR) and how deeply (tidal volume; TV) a patient is breathing. The MV signal is the product of RR and TV, i.e., MV=RR*TV. It can thus be seen that utilizing an MV sensor to measure transthoracic impedance will provide the MV, RR and TV data components necessary to perform the estimation of $MV_{AT}$ and $MV_{PEAK}$ as proposed by Kay et al.

To perform the estimation of $MV_{AT}$ and $MV_{PEAK}$, memory 230 stores historical data from the MV sensor input 260. In one embodiment, memory 230 stores historical data from the MV sensor input 260, including the MV component, the RR component and the TV component. The historical data should be in the form of a stack or queue, where each incoming data point causes the oldest data point to be discarded. Such a configuration allows efficient use of memory space. The data collection rate and the period over which data is stored are user configurable. Choice of values of the data collection rate and period will represent a compromise between reducing memory requirements and improving calculation accuracy. In one embodiment, a data collection rate of one sample per second is used. In another embodiment, a data collection rate of four samples per minute is used. In a further embodiment, a data collection period of at least about 3 minutes is used. In a still further embodiment, a data collection period of about 5 minutes is used.

Figure 5:
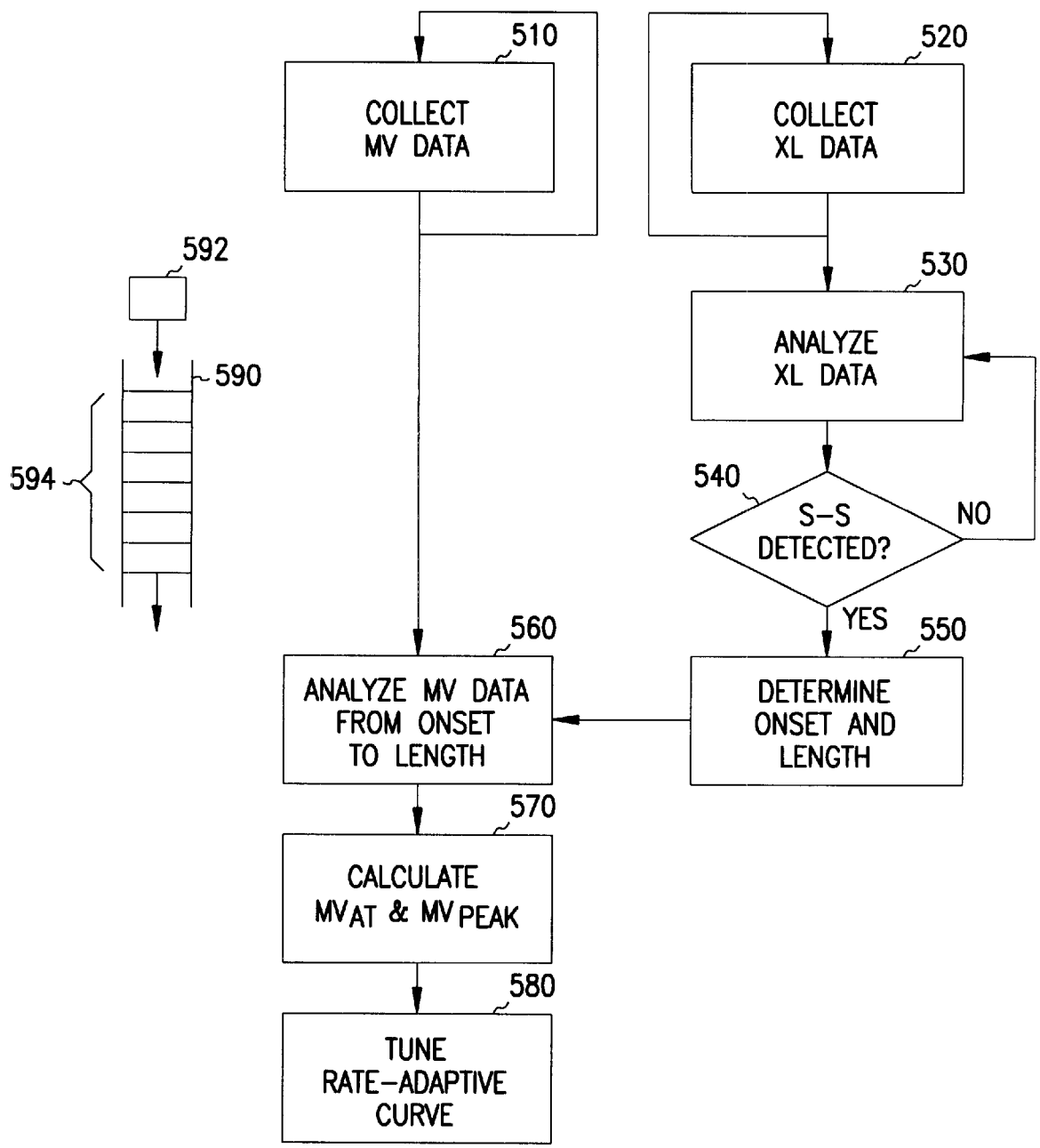
FIG. 5 is a process flowchart showing one embodiment of a method of operating a pacemaker.

FIG. 5 is a process flowchart showing one embodiment of a method of operating pacemaker 200. Action boxes 510 and 520, collecting MV data and collecting XL data, generally occur concurrently and are shown to be loops. While action boxes 510 and 520 loop for successive data input, these actions do not have to be continuous. In one embodiment, collecting MV data and collecting XL data occur periodically, e.g., at the data collection rate. In another embodiment, processor 210 of pacemaker 200 incorporates a "sleep" mode or other power-saving technique, thus pausing data collection for some period of time.

In one embodiment, collecting MV data includes receiving MV data at MV sensor input 260 and storing the MV data in memory 230. In another embodiment, collecting and storing MV data includes collecting and storing the MV component, RR component and TV component of the transthoracic impedance information generated and derived from the MV sensor. In a further embodiment, collecting XL data includes receiving XL data at XL sensor input 250 and storing the XL data in memory 230. In a still further embodiment, storing MV data and storing XL data includes placing the most recent data point in a stack and discarding the oldest data point from the stack. FIG. 5 includes a conceptual representation of a stack 590. Each data type, e.g., the MV component of the MV data, the RR component of the MV data, the TV component of the MV data, and the XL data, would generally have its own stack. Stack 590 has a size 594 corresponding to the number of data points 592 that can be stored in stack 590. The refresh rate of stack 590 is the size 594 of the stack 590 divided by data collection rate. A data point 592 in stack 590 may represent a data register. The size of the stacks, and thus the number of stored data points, will directly affect the required size of memory 230. While reducing the size of the stacks will decrease memory requirements, it will also limit the data available for calculation of $MV_{AT}$ and $MV_{PEAK}$.

The collected XL data is analyzed at action box 530. In one embodiment, analysis of collected XL data includes Fourier analysis as previously described. Analysis of collected XL data may occur each time a new data point is placed in the stack. In another embodiment, analysis of collected XL data may occur once every n data points. As an example, analysis of collected XL data may occur following collection of every 10th data point, or analysis may occur once every refresh of the stack. In a further embodiment, analysis of collected XL data may occur at regular time intervals. As an example, analysis of collected XL data may occur once every 5 minutes. In each case, analysis of collected XL data includes analysis of a sample of XL data. In one embodiment, the sample of XL data corresponds to the size of its stack.

If steady-state motion of the pacemaker is detected at decision box 540, control is transferred to action box 550 for determination of the onset of steady-state motion and the length of steady-state motion. In one embodiment, length of steady-state motion is the data collection period of the data indicative of steady-state motion. In another embodiment, length of steady-state motion is a period of time corresponding to the refresh rate of the stack. Onset of steady-state motion corresponds to the oldest data point in the sample of collected XL data indicating steady-state motion. If steady-state motion of the pacemaker is not detected at decision box 540, control is returned to action box 530 for analysis of the next sample of collected XL data.

A sample of MV data is analyzed for the changes described by Kay et al. in action box 560. The sample of MV data corresponds to the onset and length of steady-state motion determined in action box 550. In a first case, the sample of MV data corresponds to the same period of time as the sample of XL data, i.e., each MV data point in the sample corresponds in a one-to-one relationship to an XL data point and the oldest MV data point corresponds to substantially the same absolute time as the oldest XL data point where the data collection rate for MV data and XL data are substantially the same. In a second case, the sample of MV data corresponds to a period of time that has the same length as the sample of XL data, but the samples are offset in time, i.e., the oldest MV data point corresponds to an absolute time that precedes the onset of steady-state motion. In a third case, the sample of MV data corresponds to a period of time that has a length exceeding the sample of XL data and is offset in time, e.g., the length corresponding to the sample of MV data equals the length of steady-state motion plus the offset.

The first case represents an analysis of the MV data collected during the steady-state motion. The analysis will reflect the changes in the MV data as the patient is exercising. The second case represents an analysis of the MV data collected during a first period of time preceding the steady-state motion and a second period of time during the steady-state motion, where the second period of time is a portion of the length of steady-state motion. The third case represents an analysis of the MV data collected during a first period of time preceding the steady-state motion and a second period of time during the steady-state motion, where the second period of time is equal to the length of steady-state motion.

Upon analyzing the MV data in action box 560, $MV_{AT}$ and $MV_{PEAK}$ estimations are calculated in action box 570. The rate-adaptive curve is then tuned in action box 580 in response to the updated estimates of $MV_{AT}$ and $MV_{PEAK}$. Tuning of the rate-adaptive curve includes adjusting the output mapping data in response to the updated estimates of $MV_{AT}$ and $MV_{PEAK}$.

Figure 6:
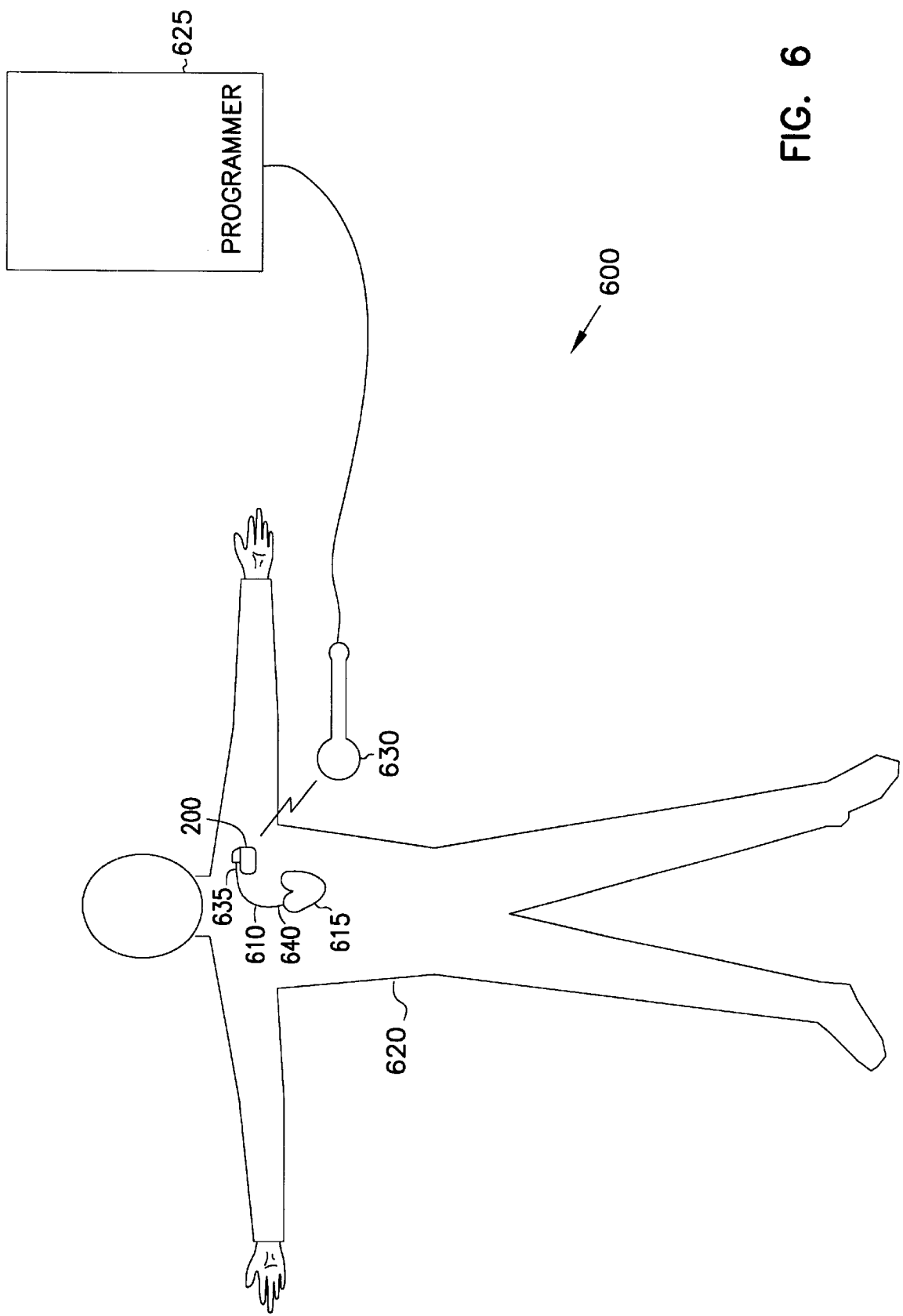
FIG. 6 is a schematic drawing of a cardiac rhythm management system.

FIG. 6 is a schematic drawing illustrating, by way of example, but not by way of limitation, one embodiment of portions of a cardiac rhythm management system 600 and an environment in which it is used. In FIG. 6, system 600 includes an implantable pacemaker 200, also referred to as an electronics unit, which is coupled by an intravascular endocardial lead 610, or other lead, to a heart 615 of patient 620. Pacemaker 200 is adapted to perform the methods as described herein. System 600 also includes an external programmer 625 providing wireless communication with pacemaker 200 using a telemetry device 630, such as might be used by a physician to initially program or periodically reprogram pacemaker 200. Endocardial lead 610 includes a proximal end 635, which is coupled to pacemaker 200, and a distal end 640, which is coupled to one or more portions of heart 615.

CONCLUSION

Tuning a rate-adaptive curve of a pacemaker in response to improved estimates of $MV_{AT}$ and $MV_{PEAK}$ results in pacing that more closely matches a patient's metabolic need. The methods and apparatus described herein facilitate estimation of $MV_{AT}$ and $MV_{PEAK}$ without external programming or maximal exercise testing, thus automating the process and reducing the amount of physician involvement required. The apparatus of the various embodiments are capable of detecting steady-state exercise of a patient with subsequent estimation of the patient's $MV_{AT}$ and $MV_{PEAK}$. Furthermore, the apparatus of the various embodiments facilitate this estimation with a simple steady-state walk of the patient, such as a walk around a park or a few minutes on a treadmill. Such apparatus thus permit improved pacing parameters with minimal inconvenience or stress to the patient.

Although specific embodiments have been illustrated and described herein, it will be appreciated by those of ordinary skill in the art that any arrangement which is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of adjusting an output mapping of a control output versus a control input for a control system, comprising:
    collecting first signal input data from a first sensor indicative of motion of the control system;
    collecting second signal input data from a second sensor;
    storing the first and second signal input data in a memory, thereby producing stored first signal input data and stored second signal input data;
    detecting steady-state motion of the system from the stored first signal input data;
    calculating at least one parameter for the output mapping in response to changes in the stored second signal input data during a period of steady-state motion, thereby producing at least one calculated parameter; and
    adjusting the output mapping in response to the at least one calculated parameter.

2. The method of claim 1, wherein collecting first signal input data from a first sensor comprises collecting first signal input data from an accelerometer.

3. The method of claim 1, wherein detecting steady-state motion of the system comprises subjecting the stored first signal input data to Fourier analysis to convert the stored first signal input data to its harmonically-related frequency components.

4. The method of claim 3, wherein detecting steady-state motion of the system comprises detecting steady-state motion when the frequency components exhibit an amplitude maxima at a frequency component in the range of about 1 to 4 Hertz.

5. The method of claim 4, wherein a power ratio of frequency components within a range of about 0.5 Hertz from the frequency component corresponding to the amplitude maxima to remaining frequency components is at least 2.

6. A method of adjusting a rate-adaptive curve of a pacemaker, comprising:
    collecting first signal input data from a first sensor indicative of motion of the pacemaker;
    collecting second signal input data from a minute ventilation sensor;
    storing the first and second signal input data in a memory, thereby producing stored first signal input data and stored second signal input data;
    detecting steady-state motion of the pacemaker from the stored first signal input data;
    calculating at least one parameter for the rate-adaptive curve in response to changes in the stored second signal input data during a period of steady-state motion, thereby producing at least one calculated parameter; and
    adjusting the rate-adaptive curve in response to the at least one calculated parameter.

7. The method of claim 6, wherein collecting first signal input data from a first sensor comprises collecting first signal input data from an accelerometer.

8. The method of claim 6, wherein detecting steady-state motion of the pacemaker comprises subjecting the stored first signal input data to Fourier analysis to convert the stored first signal input data to its harmonically-related frequency components.

9. The method of claim 8, wherein detecting steady-state motion of the pacemaker comprises detecting steady-state motion when the frequency components exhibit an amplitude maxima at a frequency component in the range of about 1 to 4 Hertz.

10. The method of claim 9, wherein a power ratio of frequency components within a range of about 0.5 Hertz from the frequency component corresponding to the amplitude maxima to remaining frequency components is at least 2.

11. The method of claim 6, wherein the at least one parameter is selected from the group consisting of minute ventilation at anaerobic threshold and minute ventilation at peak exercise.

12. The method of claim 6, wherein collecting second signal input data comprises collecting a minute ventilation data component, a respiratory rate data component and a tidal volume data component from a minute ventilation sensor.

13. A method of adjusting a rate-adaptive curve of a pacemaker, comprising:

collecting first signal input data from an accelerometer;

collecting second signal input data from a minute ventilation sensor;

storing the first and second signal input data in a memory, thereby producing stored first signal input data and stored second signal input data;

detecting steady-state motion of the pacemaker from the stored first signal input data by subjecting the stored first signal input data to Fourier analysis;

calculating at least one parameter for the rate-adaptive curve selected from the group consisting of minute ventilation at anaerobic threshold and minute ventilation at peak exercise in response to changes in the stored second signal input data during a period of steady-state motion, thereby producing at least one calculated parameter; and adjusting the rate-adaptive curve in response to the at least one calculated parameter.

14. A method of adjusting a two-slope rate-adaptive curve of a pacemaker, wherein the two-slope rate-adaptive curve is defined by parameters including minute ventilation at anaerobic threshold and minute ventilation at peak exercise, the method comprising:

collecting first signal input data from an accelerometer;

collecting second signal input data from a minute ventilation sensor;

storing the first and second signal input data in a memory, thereby producing stored first signal input data and stored second signal input data;

detecting steady-state motion of the pacemaker from the stored first signal input data by subjecting the stored first signal input data to Fourier analysis;

calculating the minute ventilation at anaerobic threshold and minute ventilation at peak exercise in response to changes in the stored second signal input data during a period of steady-state motion; and adjusting the rate-adaptive curve in response to the calculated minute ventilation at anaerobic threshold and the calculated minute ventilation at peak exercise.

15. A control system, comprising:

a processor;

a memory coupled to the processor and having output mapping data stored thereon defining an output mapping;

a regulator coupled to the processor;

a first sensor input coupled to the processor and adapted to receive first sensor input data indicative of motion of the control system;

a second sensor input coupled to the processor and adapted to receive second sensor input data;

a control output coupled to the regulator; and a detection module coupled to the processor and adapted to detect steady-state motion of the control system in response to the first sensor input data;

wherein the processor is adapted to adjust the output mapping data in response to changes in the second sensor input data when the detection module detects steady-state motion of the control system.

16. A control system, comprising:

a processor;

a memory coupled to the processor and having output mapping data stored thereon defining an output mapping;

a regulator coupled to the processor;

a first sensor input coupled to the processor;

a second sensor input coupled to the processor; and a control output coupled to the regulator;

wherein the memory has instructions stored thereon capable of causing the processor to perform a method, the method comprising collecting first signal input data from a first sensor at the first sensor input, wherein the first signal input data is indicative of motion of the control system;

collecting second signal input data from a second sensor at the second sensor input;

storing the first and second signal input data in the memory, thereby producing stored first signal input data and stored second signal input data;

detecting steady-state motion of the system from the stored first signal input data;

calculating at least one parameter for the output mapping in response to changes in the stored second signal input data during a period of steady-state motion of the system, thereby producing at least one calculated parameter; and adjusting the output mapping in response to the at least one calculated parameter.

17. A rate-adaptive pacemaker, comprising:

a processor;

a memory coupled to the processor and having output mapping data stored thereon defining a rate-adaptive curve;

a variable-rate pulse generator coupled to the processor;

a first sensor input coupled to the processor and adapted to receive first sensor input data indicative of motion of the pacemaker;

a second sensor input coupled to the processor and adapted to receive second sensor input data from a minute ventilation sensor;

a pulse output coupled to the variable-rate pulse generator; and a detection module coupled to the processor and adapted to detect steady-state motion of the pacemaker in response to the first sensor input data;

wherein the processor is adapted to adjust the output mapping data in response to changes in the second sensor input data when the detection module detects steady-state motion of the pacemaker.

18. The rate-adaptive pacemaker of claim 17, further comprising:

an accelerometer coupled to the first sensor input to provide the first sensor input data.

19. The rate-adaptive pacemaker of claim 17, wherein the detection module is adapted to detect steady-state motion of the pacemaker by subjecting the stored first signal input data to Fourier analysis to convert the stored first signal input data to its harmonically-related frequency components.

20. The rate-adaptive pacemaker of claim 19, wherein the detection module is adapted to detect steady-state motion of the pacemaker when the frequency components exhibit an amplitude maxima at a frequency component in the range of about 1 to 4 Hertz.

21. The rate-adaptive pacemaker of claim 20, wherein the detection module is adapted to detect steady-state motion of the pacemaker when a power ratio of frequency components within a range of about 0.5 Hertz from the frequency component corresponding to the amplitude maxima to remaining frequency components is at least 2.

22. A rate-adaptive pacemaker, comprising:

a processor;

a memory coupled to the processor and having output mapping data stored thereon defining a rate-adaptive curve;

a variable-rate pulse generator coupled to the processor;

a first sensor input coupled to the processor;

a second sensor input coupled to the processor; and a pulse output coupled to the variable-rate pulse generator;

wherein the memory has instructions stored thereon capable of causing the processor to perform a method, the method comprising:

collecting first signal input data from a first sensor indicative of motion of the pacemaker at the first sensor input;

collecting second signal input data from a minute ventilation sensor at the second sensor input;

storing the first and second signal input data in the memory, thereby producing stored first signal input data and stored second signal input data;

detecting steady-state motion of the pacemaker from the stored first signal input data;

calculating at least one parameter for the rate-adaptive curve in response to changes in the stored second signal input data during a period of steady-state motion, thereby producing at least one calculated parameter; and adjusting the output mapping data in response to the at least one calculated parameter.

23. The rate-adaptive pacemaker of claim 22, wherein collecting first signal input data from a first sensor comprises collecting first signal input data from an accelerometer.

24. The rate-adaptive pacemaker of claim 22, wherein detecting steady-state motion of the pacemaker comprises subjecting the stored first signal input data to Fourier analysis to convert the stored first signal input data to its harmonically-related frequency components.

25. The rate-adaptive pacemaker of claim 24, wherein detecting steady-state motion of the pacemaker comprises detecting steady-state motion when the frequency components exhibit an amplitude maxima at a frequency component in the range of about 1 to 4 Hertz.

26. The rate-adaptive pacemaker of claim 25, wherein a power ratio of frequency components within a range of about 0.5 Hertz from the frequency component corresponding to the amplitude maxima to remaining frequency components is at least 2.

27. The rate-adaptive pacemaker of claim 22, wherein the at least one parameter is selected from the group consisting of minute ventilation at anaerobic threshold and minute ventilation at peak exercise.

28. The rate-adaptive pacemaker of claim 22, wherein collecting second signal input data comprises collecting a minute ventilation data component, a respiratory rate data component and a tidal volume data component from a minute ventilation sensor.

29. A method of adjusting a rate-adaptive curve of a pacemaker for use with a patient, comprising:

collecting first signal input data from a first sensor indicative of exercise of the patient;

collecting second signal input data from a minute ventilation sensor;

storing the first and second signal input data in a memory, thereby producing stored first signal input data and stored second signal input data;

detecting steady-state exercise of the patient from the stored first signal input data;

calculating at least one parameter for the rate-adaptive curve in response to changes in the stored second signal input data during a period of steady-state exercise, thereby producing at least one calculated parameter; and adjusting the rate-adaptive curve in response to the at least one calculated parameter.

30. A rate-adaptive pacemaker for use with a patient, comprising:

a processor;

a memory coupled to the processor and having output mapping data stored thereon defining a rate-adaptive curve;

a variable-rate pulse generator coupled to the processor;

a first sensor input coupled to the processor and adapted to receive first sensor input data indicative of exercise of the patient;

a second sensor input coupled to the processor and adapted to receive second sensor input data from a minute ventilation sensor;

a pulse output coupled to the variable-rate pulse generator; and a detection module coupled to the processor and adapted to detect steady-state exercise of the patient in response to the first sensor input data;

wherein the processor is adapted to adjust the output mapping data in response to changes in the second sensor input data when the detection module detects steady-state exercise of the patient.

* * * * *